United States Patent
Sode et al.

(10) Patent No.: US 11,293,921 B2
(45) Date of Patent: Apr. 5, 2022

(54) DIRECT ELECTRON TRANSFER-TYPE OXIDOREDUCTASE-MODIFIED MOLECULAR RECOGNITION ELEMENT

(71) Applicants: ARKRAY, Inc., Kyoto (JP); Ultizyme International Ltd., Tokyo (JP)

(72) Inventors: Koji Sode, Tokyo (JP); Yuka Takahashi, Tokyo (JP); Junko Shimazaki, Tokyo (JP); Masashi Tsukada, Kyoto (JP); Yosuke Murase, Kyoto (JP)

(73) Assignees: ARKRAY, Inc., Kyoto (JP); Ultizyme International Ltd., Tokyo (JP)

( * ) Notice: Subject to any disclaimer, the term of this patent is extended or adjusted under 35 U.S.C. 154(b) by 0 days.

(21) Appl. No.: 16/590,539

(22) Filed: Oct. 2, 2019

(65) Prior Publication Data

US 2020/0110080 A1 Apr. 9, 2020

(30) Foreign Application Priority Data

Oct. 3, 2018 (JP) .............................. JP2018-188675

(51) Int. Cl.
  *G01N 33/543* (2006.01)
  *C07K 16/18* (2006.01)
  *G01N 27/327* (2006.01)

(52) U.S. Cl.
  CPC ......... *G01N 33/5438* (2013.01); *C07K 16/18* (2013.01); *C12Y 101/9901* (2013.01); *G01N 27/3277* (2013.01); *C07K 2317/622* (2013.01); *C07K 2319/61* (2013.01)

(58) Field of Classification Search
  CPC ........... G01N 33/5438; G01N 27/3277; G01N 33/573; C07K 16/18; C07K 2317/622; C07K 2319/61; C07K 16/2818; C07K 2319/01; C12Y 101/9901; C12Y 101/01047; C12N 9/0006; C12Q 1/68
  See application file for complete search history.

(56) References Cited

U.S. PATENT DOCUMENTS

| 5,736,188 A | 4/1998 | Alcock et al. | |
| 5,866,321 A * | 2/1999 | Matsue | .................. C12Q 1/001 435/5 |
| 2004/0023330 A1* | 2/2004 | Sode | ...................... C12N 1/205 435/69.1 |

(Continued)

FOREIGN PATENT DOCUMENTS

| EP | 0992794 A2 | 4/2000 |
| EP | 1661516 A1 | 5/2006 |

(Continued)

OTHER PUBLICATIONS

Varga et al., Draft Genome Sequence Dtermination for Cystic Fibrosis and Chronic Granulomatous Disease Burkholderia multivorans Isolates, Journals American Society for Microbiology, vol. 194, No. 22, pp. 6356-6357. (Year: 2012).*

(Continued)

*Primary Examiner* — Melanie Brown
(74) *Attorney, Agent, or Firm* — Morgan, Lewis & Bockius LLP

(57) ABSTRACT

A molecular recognition element comprising a target molecule-recognizing portion, and a direct electron transfer-type oxidoreductase linked to the target molecule-recognizing portion.

8 Claims, 7 Drawing Sheets

Specification includes a Sequence Listing.

(56) References Cited

U.S. PATENT DOCUMENTS

| | | | | |
|---|---|---|---|---|
| 2006/0160100 A1* | 7/2006 | Gao | ............... | C12Q 1/6825 |
| | | | | 435/6.11 |
| 2011/0073493 A1* | 3/2011 | Chatelier | ......... | G01N 33/54326 |
| | | | | 205/777.5 |
| 2018/0164303 A1* | 6/2018 | Hu | ............ | G01N 33/549 |
| 2018/0355022 A1* | 12/2018 | Masakari | ............ | C07K 19/00 |
| 2020/0165579 A1* | 5/2020 | Alfonta | ............ | G01N 27/3271 |

FOREIGN PATENT DOCUMENTS

| | | |
|---|---|---|
| JP | 2018-154579 A | 10/2018 |
| WO | 2017/094776 | * 11/2016 |
| WO | 2018/073588 A1 | 4/2018 |

OTHER PUBLICATIONS

Mattiasson et al., "An Enzyme Immunoelectrode: Assay of human serum albumin and insulin," FEBS Letters, 78: 251-254(1977).

Extended European Search Report issued in counterpart European Patent Application No. 19201172.4 dated Mar. 24, 2020.

Kimura et al., "Convenient and University Fabrication Method for Antibody-Enzyme Complexes as Sensing Elements Using the SpyCatcher/SpyTag System," Analytical Chemistry, 90 (24): 14500-14506 (2018).

Yoshida et al., "X-ray structure of the direct electron transfer-type FAD glucose dehydrogenase catalytic subunit complexed with a hitchhiker protein," Acta Crystallographica/Section D, Biological Crystallography, 75 (9): 841-851 (2019).

* cited by examiner

DIRECT ELECTRON TRANSFER-TYPE OXIDOREDUCTASE-MODIFIED MOLECULAR RECOGNITION ELEMENT

SEQUENCE LISTING SUBMISSION VIA EFS-WEB

A computer readable text file, entitled "SequenceListing.txt," created on or about Oct. 2, 2019 with a file size of about 28 kb contains the sequence listing for this application and is hereby incorporated by reference in its entirety.

TECHNICAL FIELD

The present invention relates to a novel molecular recognition element that can be used for biosensing technology such as an immunosensor.

BACKGROUND ART

In a conventional immunoassay such as ELISA using an antibody labeled with an enzyme, or the like, it is necessary to separate (Bound/Free (B/F) separation) an antibody not bound to an antigen by performing a washing operation such as lateral flow after a reaction between an antigen and an antibody in order to remove a nonspecific signal. However, such a B/F separation operation complicates the procedures and the efficiency of the B/F separation may affect the signal accuracy.

As the enzyme used for labeling an antibody, a peroxidase, and an alkali phosphatase are often used. In Non-Patent Literature 1, an electrochemical type immunoassay using an antibody labeled with a glucose oxidase (GOD) is disclosed.

CITATION LIST

[Non-Patent Literature 1] FEBS LETTERS, June 1977 DOI: 10.1016/0014-5793 (77) 80317-7

SUMMARY OF INVENTION

In the method disclosed in Non-Patent Literature 1, electrons generated by a reaction of the GOD and a substrate are converted to a hydrogen peroxide, and the hydrogen peroxide diffuses into the solution and is reduced on the surface of an electrode to generate a signal. Therefore, in the reaction system, a signal that would be generated by an antibody-GOD existing in the vicinity of the electrode due to nonspecific adsorption, etc. becomes a noise, and therefore it is required to undergo a careful cleaning step. In addition, when nonspecific adsorption is strong, or an antigen, which is the target molecule, has been adsorbed nonspecifically, it is difficult to completely remove the nonspecific signal. Further, depending on the environment between the GOD bound to the antibody and the electrode, there is a limitation on removing noise components by washing.

One aspect of the invention is to provide a novel molecular recognition element that can be used in biosensing technology such as an immunosensor.

According to an embodiment of the invention, a molecular recognition element comprising a target molecule-recognizing portion, and a direct electron transfer-type oxidoreductase linked to the target molecule-recognizing portion is provided.

According to another embodiment of the invention, the molecular recognition element, wherein the target molecule-recognizing portion comprises a target molecule-recognizing protein, is provided.

According to another embodiment of the invention, the molecular recognition element, wherein a target molecule is an antigen and the target molecule-recognizing portion is an antibody against the antigen, is provided.

According to another embodiment of the invention, the molecular recognition element, wherein the direct electron transfer-type oxidoreductase is an oxidoreductase comprising an electron-transferring domain, or an electron-transferring subunit, is provided.

According to another embodiment of the invention, the molecular recognition element, wherein the electron-transferring domain is a heme-containing domain, or the electron-transferring subunit is a heme-containing subunit, is provided.

According to another embodiment of the invention, the molecular recognition element, wherein the oxidoreductase is a glucose dehydrogenase, is provided.

According to another embodiment of the invention, the molecular recognition element, wherein the target molecule-recognizing portion and the direct electron transfer-type oxidoreductase are linked by a cross-linker, is provided.

According to another embodiment of the invention, the molecular recognition element, wherein the molecular recognition element comprises a fusion protein of the target molecule-recognizing portion and the direct electron transfer-type oxidoreductase, is provided.

According to another embodiment of the invention, a sensor comprising an electrode, and the aforedescribed molecular recognition element immobilized on the electrode, is provided.

According to another embodiment of the invention, the sensor wherein the molecular recognition element is immobilized on the electrode by means of a monolayer forming molecule, is provided.

According to another embodiment of the invention, a method for measuring a target molecule comprising introducing a sample containing a target molecule into the aforedescribed sensor; and detecting a signal based on the target molecule, is provided.

According to another embodiment of the invention, a reagent for measuring a target molecule comprising the aforedescribed molecular recognition element, is provided.

According to an embodiment of the present invention, a molecular recognition element capable of directly transferring electrons to an electrode can be constructed by linking a direct electron transfer-type oxidoreductase to a molecular recognition portion such as an antibody.

Since a direct electron transfer signal can be detected based on the occurrence of the specific antigen-antibody binding, a system of measurement that is not affected by nonspecific binding, and does not require a careful washing operation can be constructed.

From the above, construction of an electrochemical immunosensor free from the influence of nonspecific adsorption can be expected.

DESCRIPTION OF EMBODIMENTS

<Molecular Recognition Element>

Figure 1:
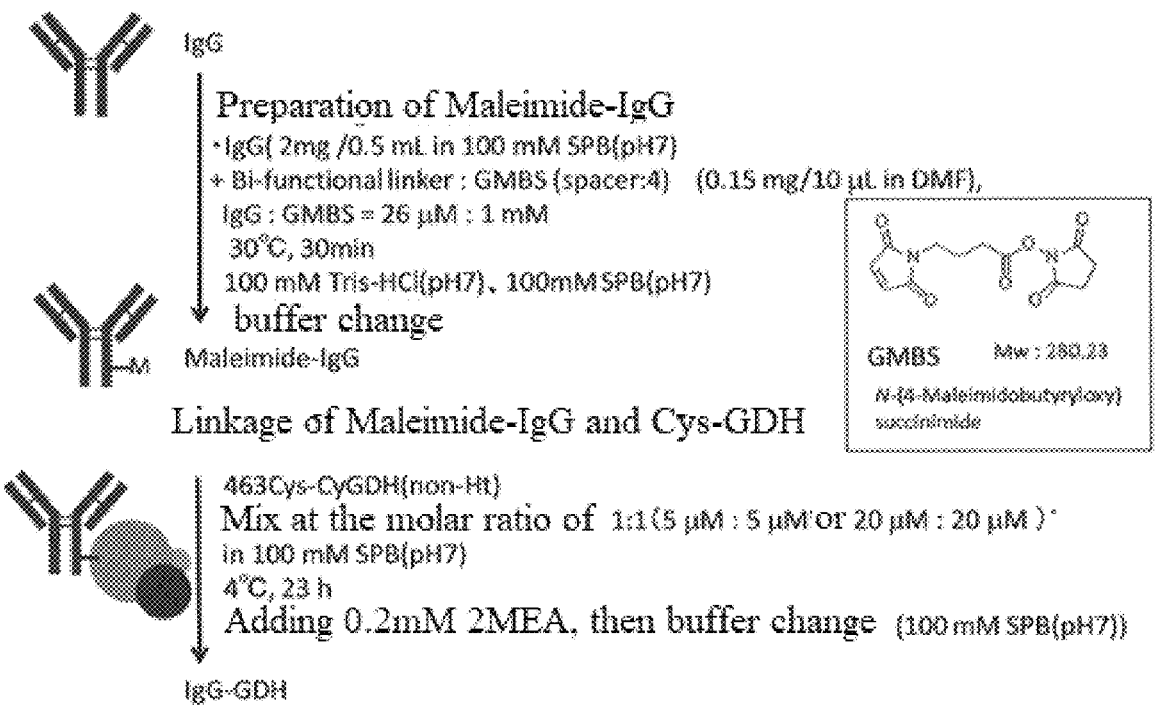
FIG. 1 shows a cross-linking procedure of anti-CRP IgG and GDH.

The molecular recognition element comprises a target molecule-recognizing portion, and a direct electron transfer-type oxidoreductase linked to the target molecule-recognizing portion. Hereinafter, it may be referred to as the "molecular recognition element of the present invention".

<Target Molecule>

There is no particular limitation on the type of target molecule, and examples thereof include a low molecular weight compound, a peptide, a protein, a hormone, a sugar, a toxin, a viral particle, and a metal.

<Target Molecule-Recognizing Portion>

A target molecule-recognizing portion can be selected according to the type of the target molecule, and examples thereof include an antibody capable of recognizing an antigen, which is the target molecule; a target molecule-recognizing protein such as a receptor protein capable of recognizing a hormone, which is the target molecule; a nucleic acid aptamer capable of recognizing a low molecular weight compound or a peptide, which is the target molecule; and a lectin capable of recognizing a sugar, which is the target molecule. Recognizing the target molecule includes binding to the target molecule.

When the target molecule-recognizing portion is a protein it preferably has at least 50 amino acids, e.g. at least 100 or 250 amino acids. For example it may have 50-500 amino acids. When the target molecule-recognizing portion is an antibody, the antibody may be IgG, IgE or IgA, a half antibody, or a single-chain antibody (scFv). Furthermore, it may be a partial fragment of the antibody. Such fragments retain their ability to recognize their target molecule.

<Direct Electron Transfer-Type Oxidoreductase>

A "direct electron transfer-type oxidoreductase" means a type of oxidoreductase capable of transferring an electron directly between an enzyme and an electrode. In the case of using the direct electron transfer-type oxidoreductase, electrons generated by the reaction can be transferred directly between the enzyme and the electrode without involvement of a redox substance, such as an artificial electron acceptor (electron-transferring mediator) e.g. redox molecules.

The direct electron transfer-type oxidoreductase may include an electron-transferring subunit or an electron-transferring domain. Examples of the electron-transferring subunit include a subunit containing heme, and examples of the electron-transferring domain include a heme-containing domain. Examples of the heme-containing subunit, or domain include a subunit or a domain containing heme c or heme b, and more specifically, a subunit or a domain containing cytochrome such as cytochrome c, or cytochrome b.

As an oxidoreductase having a domain containing heme C, for example, a fusion protein of PQQ glucose dehydrogenase (PQQGDH) and cytochrome c as disclosed in International Publication No. WO 2005/030807 can be used.

Further, a cholesterol oxidase, and a quinoheme ethanol dehydrogenase can also be used.

Meanwhile, as an oxidoreductase including a heme-containing subunit, an oligomeric enzyme having at least a catalytic subunit and a heme-containing subunit is preferably used.

A large number of oligomeric-type oxidoreductases including a heme-containing subunit are known, and examples thereof include glucose dehydrogenase (GDH), sorbitol dehydrogenase (sorbitol DH), D-fructose dehydrogenase (fructose DH), D-glucoside-3-dehydrogenase (glucoside-3-dehydrogenase), cellobiose dehydrogenase, and lactate dehydrogenase.

Among them, glucose dehydrogenase (GDH) is preferable, and the catalytic subunit of GDH can contain flavin adenine dinucleotide (FAD).

An example of the GDH having a catalytic subunit containing FAD is a GDH derived from *Burkholderia cepacia*. An example of the amino acid sequence of the catalytic subunit (α subunit) is shown as SEQ ID NO: 3. The catalytic subunit may have a mutation, such as substitution, deletion, and insertion. Examples of a mutant of the catalytic subunit of FAD-dependent GDH derived from *Burkholderia cepacia* include a mutant in which amino acid residues at positions 472 and 475 are substituted (WO 2005/103248), a mutant in which amino acid residues at positions 326, 365 and 472 are substituted (Japanese Patent Laid-Open No. 2012-090563), and a mutant substituted at positions 365 as well as 326, 472, 475, 529, etc. (WO 2006/137283). In a further preferred aspect the GDH has a mutant at position 463 (to cysteine) in the catalytic subunit, as used in the Examples described herein. However, the mutant is not limited to these, and may contain mutations at other positions. Thus in a preferred aspect the GDH comprises a catalytic subunit having an amino acid sequence as set forth in SEQ ID NO: 3 or a sequence with up to 10 mutations, e.g. 1, 2, 3, 4 or 5 mutations. Such mutations include substitutions, deletions and insertions (preferably of a single amino acid only), preferably as described above.

There is no particular limitation on the type of a heme-containing subunit, and examples thereof include a cytochrome-containing subunit (β subunit) of a GDH derived from *Burkholderia cepacia*; and an example of its amino acid sequence is shown as SEQ ID NO: 4. The cytochrome-containing subunit may have a mutation such as substitution, deletion, insertion, etc. Thus in a preferred aspect the GDH comprises a cytochrome-containing subunit having an amino acid sequence as set forth in SEQ ID NO: 4 or a sequence with up to 10 mutations, e.g. 1, 2, 3, 4 or 5 mutations. Such mutations include substitutions, deletions and insertions (preferably of a single amino acid only).

GDH may be an oligomer constituting the above-mentioned catalytic subunit and a cytochrome-containing subunit, but may also include a regulatory subunit in addition to the catalytic subunit and cytochrome-containing subunit. An example of the amino acid sequence of the regulatory subunit (γ subunit) of a GDH derived from *Burkholderia cepacia* is shown as SEQ ID NO: 2. However, the γ subunit may have a mutation, such as substitution, deletion, or insertion. Thus in a preferred aspect the GDH comprises a regulatory subunit having an amino acid sequence as set forth in SEQ ID NO: 2 or a sequence with up to 10 mutations, e.g. 1, 2, 3, 4 or 5 mutations. Such mutations include substitutions, deletions and insertions (preferably of a single amino acid only).

As an example, the nucleotide sequence of a chromosomal DNA fragment including the GDH γ subunit gene, a subunit gene, and f3 subunit gene of the *Burkholderia cepacia* KS1 strain is shown as SEQ ID NO: 1. Three open reading frames (ORFs) are present in the nucleotide sequence, and the first ORF from the 5'-end side (nucleotide numbers 258-761) encodes the γ subunit (SEQ ID NO: 2), the second ORF (nucleotide numbers 764-2380) encodes the α subunit (SEQ ID NO: 3), and the third ORF (nucleotide numbers 2386-3660) encodes the β subunit (SEQ ID NO: 4). Thus in a preferred aspect the GDH comprises an α and β subunit, and optionally a γ subunit, encoded, respectively, by a nucleotide sequence as set forth in SEQ ID NO: 3, 4 and 2 (or collectively as set forth in SEQ ID NO: 1) or a sequence with up to 10 mutations, e.g. 1, 2, 3, 4 or 5 mutations. Such mutations include substitutions, deletions and insertions (preferably which result in mutation of a single amino acid only in the encoded sequence), preferably as described hereinbefore.

<Linkage of Target Molecule-Recognizing Portion and Direct Electron Transfer-Type Oxidoreductase>

Although there is no particular limitation on the method of linking a target molecule-recognizing portion and a direct electron transfer-type oxidoreductase insofar as the target molecule-recognizing capability of the target molecule-recognizing portion, and the enzyme activity of the direct electron transfer-type oxidoreductase are not significantly retarded, it is preferable that the target molecule-recognizing portion and the direct electron transfer-type oxidoreductase are linked with a covalent bond(s). In an embodiment, the target molecule-recognizing portion and the direct electron transfer-type oxidoreductase are linked with a cross-linker.

A target molecule-recognizing portion and a direct electron transfer-type oxidoreductase can be linked, for example, by introducing a cross-linker (crosslinkable reactive group) into the target molecule-recognizing portion, and by reacting a reactive functional group, such as a thiol group, an amino group, and a carboxyl group, possessed by the direct electron transfer-type oxidoreductase with the cross-linker so that the two are cross-linked.

Further, a target molecule-recognizing portion and a direct electron transfer-type oxidoreductase can be linked, for example, by introducing a cross-linker (crosslinkable reactive group) into the direct electron transfer-type oxidoreductase, and by reacting a reactive functional group, such as a thiol group, an amino group, and a carboxyl group, possessed by the target molecule-recognizing portion with the cross-linker so that the two are cross-linked.

The reactive functional group may be a functional group originally possessed by a target molecule-recognizing portion or a direct electron transfer-type oxidoreductase, or may be a functional group artificially introduced by amino acid substitution, amino acid introduction, or the like. In addition, the reactive functional group may be a plurality of unspecified functional groups, such as amino groups present in a protein, or one to several specified functional groups such as thiol groups present in a protein.

For example, when a target molecule-recognizing portion is an IgG antibody, examples of the above may include a thiol group in a half antibody (rIgG) generated by reducing an antibody (IgG), and with respect to a direct electron transfer-type oxidoreductase, examples of the above may include a thiol group of a cysteine residue present in the amino acid sequence of the direct electron transfer-type oxidoreductase.

As a cross-linker, a publicly known cross-linker can be used. Examples of a cross-linker that reacts with a thiol group include a maleimide compound, a haloacetic acid compound, a pyridyl disulfide compound, a thiosulfone compound, and a vinyl sulfone compound. Meanwhile, examples of a cross-linker that reacts with an amino group include an N-hydroxysuccinimide (NHS) ester compound, an imido ester compound, a pentafluorophenyl ester compound, and a hydroxymethyl phosphine compound. Further, examples of a cross-linker that reacts with a carboxyl group include an oxazoline compound. In a preferred aspect the cross-linker is GMBS as described in the Examples.

In another embodiment, by forming a fusion protein of a target molecule-recognizing portion and a direct electron transfer-type oxidoreductase, the two are linked together.

The fusion protein may be formed, for example, by constructing a gene construct in which a nucleotide sequence encoding a direct electron transfer-type oxidoreductase, and a nucleotide sequence encoding a target molecule-recognizing portion are linked such that the two are translated by combining the respective reading frames to be expressed as a fusion protein of the target molecule-recognizing portion, and the direct electron transfer-type oxidoreductase; and then making an appropriate host express the gene construct. Either of the target molecule-recognizing portion or the direct electron transfer-type oxidoreductase may be on the N-terminal side of the fusion protein. Alternatively, the two may be linked via an appropriate peptide linker. Furthermore, a tag sequence for detection or purification may be added to a fusion protein.

A nucleotide sequence encoding a direct electron transfer-type oxidoreductase may be appropriately selected corresponding to the type of the direct electron transfer-type oxidoreductase, and a known sequence can be utilized. Examples thereof include the nucleotide sequence encoding a GDH derived from the aforedescribed *Burkholderia cepacia*. Such sequences are described hereinbefore.

Also, a nucleotide sequence encoding a target molecule-recognizing portion may be appropriately selected corresponding to the type of the target molecule-recognizing portion and a known sequence such as a nucleotide sequence encoding an antibody can be utilized. Examples of the nucleotide sequence encoding an anti-CRP single-chain antibody include the sequence described in Journal of Bioscience and Bioengineering, Volume 105, Issue 3, March 2008, Pages 261-272.

Preparation, expression in a host, purification, and the like of a DNA encoding a fusion protein can be performed by a known genetic recombination technique.

<Sensor>

A sensor according to an embodiment of the present invention includes an electrode and a molecular recognition element immobilized on the electrode. Since a direct electron transfer-type oxidoreductase is used, a structure without an electron-transferring mediator as described above is possible.

As the electrode, an electrode composed of a known electrode material is considered, and examples thereof include a gold electrode, a platinum electrode, and a carbon electrode.

The sensor includes an electrode, on which the molecular recognition element of the present invention is immobilized, as a working electrode, and it may further include a counter electrode (platinum, etc.) and/or a reference electrode (Ag/AgCl, etc.).

The sensor may further include a constant-temperature cell for receiving a test sample, a power supply for applying a voltage to the working electrode, an ammeter, a recorder, and the like.

The structure of such an enzyme sensor is well known in the relevant art, and described, for example, in "Biosensors-Fundamental and Applications", Anthony P. F. Turner, Isao Karube, and Geroge S. Wilson; Oxford University Press 1987.

In immobilizing the molecular recognition element of the present invention on an electrode, it is necessary to immobilize the molecular recognition element on the electrode in a state where the oxidoreductase included in the molecular recognition element is placed close to the electrode so that the oxidoreductase can function as a direct electron transfer-type oxidoreductase. In this regard, it is said that the distance limit allowing direct electron transfer in a physiological reaction system is 1 to 2 nm. Therefore, it is preferable to place the element such that the distance between the oxidoreductase molecule and the electrode becomes 1 to 2 nm or less in order not to compromise the electron transfer from the oxidoreductase to the electrode.

There is no particular restriction on the method of immobilization, and its examples include a method of chemically immobilizing the molecular recognition element on the electrode with a cross-linker, or the like, a method of indirectly immobilizing the molecular recognition element on the electrode using a binder, or the like, and a method of physically adsorbing the molecular recognition element on the electrode.

As a method of chemically immobilizing the molecular recognition element on the electrode with a cross-linker, or the like, a method of directly immobilizing the molecular recognition element on the electrode may be used, and additionally, for example, there is a method as disclosed in Japanese Patent Laid-Open No. 2017-211383. It is a method in which a monolayer (self-assembled monolayer (SAM)) forming molecule is immobilized on the electrode, and the molecular recognition element is immobilized by means of the SAM forming molecule.

A monolayer forming molecule is a compound capable of binding to an electrode, and capable of binding the molecular recognition element, and is a compound capable of forming a monolayer when a plurality of the molecules are unidirectionally bound on the electrode surface. By using a monolayer forming molecule, the distance between the electrode and the enzyme molecule can be controlled.

The monolayer forming molecule preferably has a first functional group having affinity for the electrode, a spacer site, and a second functional group capable of reacting with a functional group of the molecular recognition element. More preferably it has a structure where the first functional group having affinity for the electrode is bound to the first end of the spacer site, and the second functional group capable of reacting with the functional group of the molecular recognition element is bound to the second end of the spacer site. Examples of the first functional group having affinity for the electrode include, when the electrode is metallic, a thiol group, and a dithiol group, and when the electrode is carbon, pyrene, and porphyrin.

Examples of the second functional group capable of reacting with a functional group of the molecular recognition element include a succinimide group when it is reacted with an amino group of the molecular recognition element (including the terminal amino group and the side chain amino group), and an oxazoline group when it is reacted with a carboxyl group of the molecular recognition element (including a terminal carboxyl group and a side chain carboxyl group).

Examples of a monolayer forming molecule having a thiol group, or a dithiol group include compounds having the following structures.

In this regard, L is a spacer, and X is a functional group capable of reacting with a functional group of the molecular recognition element. Examples thereof include a succinimide or its ester and a thiol. Examples of the type of spacer include alkylene having 1 to 20 (e.g. 3 to 7) carbon atoms, alkenylene having 1 to 20 (e.g. 3 to 7) carbon atoms, alkynylene having 1 to 20 (e.g. 3 to 7) carbon atoms, polyethylene glycol having a polymerization degree of 2 to 50, and an oligopeptide having 1 to 20 amino acid residues, or combinations of such spacers. In the alkylene, alkenylene, or alkynylene, one or more —CH$_2$— may be replaced by —O—.

Examples of such a compound include the following DSH.

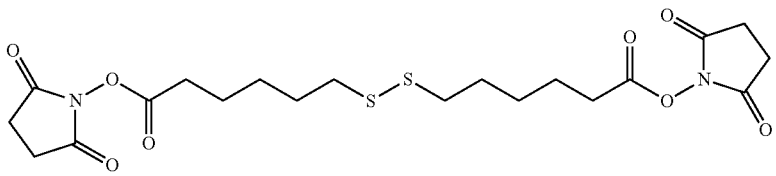

Dithiobis(succinimidyl hexanoate):DSH

Examples of a monolayer forming molecule having, for example, pyrene or porphyrin include a compound having the following structure.

In this regard, Py stands for pyrene, Po for porphyrin, L for a spacer, and X for a functional group capable of reacting with the functional group of the enzyme molecule. Examples of the type of the spacer include alkylene having 1 to 20 carbon atoms, alkenylene having 1 to 20 carbon atoms, alkynylene having 1 to 20 carbon atoms, polyethylene glycol having a polymerization degree of 2 to 50, and an oligopeptide having 1 to 20 amino acid residues.

$$Py\text{-}L\text{-}X \quad (3)$$

$$Po\text{-}L\text{-}X \quad (3')$$

Examples of a monolayer forming molecule having, for example, pyrene include a compound having the following structure.

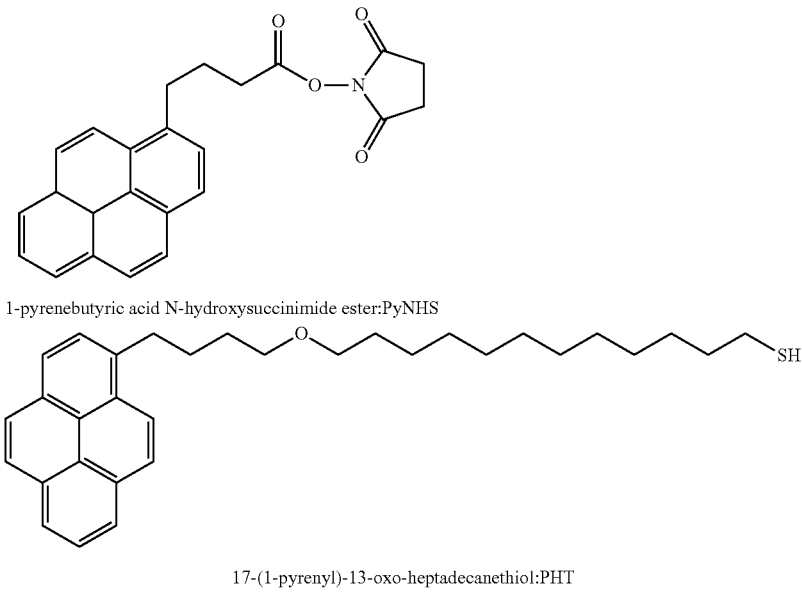

1-pyrenebutyric acid N-hydroxysuccinimide ester:PyNHS 17-(1-pyrenyl)-13-oxo-heptadecanethiol:PHT <Method of Measuring Target Molecule>

A method of measuring a target molecule according to an embodiment of the present invention comprises introducing a sample containing a target molecule into the sensor, and detecting a signal based on the target molecule.

There is no particular limitation on the sample, insofar as it is a sample containing a target molecule, and it is preferably a tissue-derived sample. Examples thereof include a sample obtained from blood, a sample obtained from urine, a cell extract sample, and a cell culture liquid.

There is no particular limitation on the step of introducing a sample into a sensor, and examples thereof include adding a sample liquid onto the sensor, and dipping the sensor in a sample liquid.

The current value, potential value such as open circuit potential or resistance value such as impedance, which is associated with the direct electron transfer reaction caused by an oxidation-reduction reaction of a substrate when an enzyme reaction occurs in the vicinity of the electrode, greatly changes in the molecular recognition element of the present invention before and after the target molecule binds to the target molecule-recognizing portion. Therefore, the target molecule can be detected and quantified by detecting this change in the current value, potential value such as open circuit potential or resistance value such as impedance as a signal.

For example, in the case where the molecular recognition element of the present invention is a complex of an antibody and CyGDH (cytochrome GDH), and a sensor in which the complex is immobilized on the electrode is used, when a sample containing an antigen is added to the sensor, the antigen is bound to the antibody and the direct electron transfer ability of CyGDH changes. At this time, if glucose, which is a substrate of CyGDH, is added, an enzyme reaction occurs, and electrons generated therefrom are transferred to the electrode through heme to flow a current according to the amount of the antigen. Therefore, the amount of the antigen can be measured by measuring this current value.

In the measurement method of the present invention, since the concentration of a target molecule is detected by a current value based on direct electron transfer, there are advantages that a nonspecific signal can be suppressed, and B/F separation such as a washing step can be omitted.

<Reagent for Measuring Target Molecule>

The reagent for measuring a target molecule of the present invention includes the molecular recognition element of the present invention.

The reagent for measuring a target molecule may further contain a reaction substrate, a reaction buffer, or the like.

When analyzing a target molecule such as an antigen in a sandwich method, a target molecule binding substance different from the target molecule binding site included in the molecular recognition element of the present invention may be included.

For example, an antibody that binds to the target molecule (antigen) is prepared, and immobilized on the electrode.

A sample containing a target molecule is added to the electrode, on which the antibody is immobilized, to allow the target molecule to bind to the antibody (first antibody) on the electrode.

Then the molecular recognition element of the present invention comprising an antibody (second antibody) against the antigen and the direct electron transfer-type oxidoreductase linked thereto is added thereto to form a complex of the first antibody/the antigen/the second antibody/the oxidoreductase on the electrode. In other words, an oxidoreductase is recruited in the vicinity of the electrode according to the abundance of the antigen. By making the oxidoreductase react with the substrate there, an oxidation-reduction reaction occurs, and the electrons generated thereby are transferred between the electron-transferring site, or the electron-transferring subunit of the oxidoreductase and the electrode so that a current flows according to the abundance of the antigen. Therefore, the target molecule can be detected and quantified by measuring this current value, potential value such as open circuit potential or resistance value such as impedance. In other words, in contrast to the heretofore known immunoassay using an enzyme as a labeling agent, since the detection in principle relies on the measurement based on the direct electron transfer reaction, and the molecular recognition element which is not bound with the antigen and is free in the solution, is not present in the vicinity of the electrode to send out a signal, only the molecular recognition element, which is bound with the antigen, sends out a signal. Therefore, the treatment for eliminating nonspecific adsorption such as a washing operation can be greatly reduced as compared with the conventional method.

EXAMPLES

Next, the present invention will be more specifically described with reference to Examples. The present invention is not restricted in any way by these Examples.

Example 1

A CyGDH derived from *B. cepacia* was used as the GDH including a cytochrome c-containing subunit. The CyGDH derived from *B. cepacia* is an oligomeric enzyme constituted of 3 subunits of γ, α and β, and these 3 subunits are encoded by the gene having the nucleotide sequence of SEQ ID NO: 1.

In the present Example, a mutant was used, in which the amino acid residue at the 463-th position of the α subunit was substituted with a cysteine residue to be used for binding to IgG. Specifically, for the plasmid pTrc99Aγαβ for expressing GDH described in Japanese Patent Laid-Open No. 2012-090563, pTrc99Aγα(463C)β in which a mutation was introduced into the α subunit was used to express a mutated GDH. This was used in the following experiment.

By cross-linking the $NH_2$ group of an antihuman CRP (C Reactive Protein) monoclonal antibody (mouse CRP-MCA, (Oriental Yeast Co., Ltd.), hereinafter IgG) and the SH group of a cysteine residue introduced into the α subunit of the cytochrome c-containing GDH produced as above using the cross-linker GMBS (Dojindo Molecular Technologies, Inc.), an IgG-GDH complex was produced. The specific procedure is shown in FIG. 1.

Figure 2:
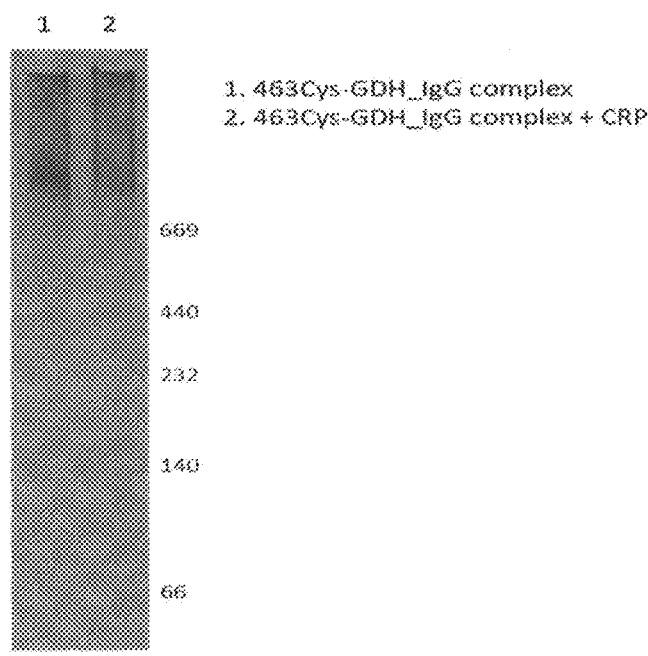
FIG. 2 shows the result of polyacrylamide gel electrophoresis for confirming the interaction between IgG-GDH and CRP (photograph).

The CRP binding ability of the obtained IgG-GDH complex was examined by polyacrylamide gel electrophoresis and activity staining. The results are shown in FIG. 2. Comparing lane 1 (without CRP) and lane 1 (with CRP addition), the band near 800 kDa of lane 2 became thinner. This is conceivably because the molecular weight of the IgG-GDH complex was shifted to the higher molecular weight site due to binding of CRP to IgG, which indicated that the IgG-GDH complex was able to bind CRP.

Next, the above-described IgG-GDH complex was immobilized on the gold wire electrode whose surface was modified with a SAM-forming molecule (DSH).

The procedure is as follows.

TABLE 1

| Electrode | Au wire (φ 0.5 mm, 6-7 cm) |
|---|---|
| Preparation of Enzyme electrode | Cleaning of Au surface<br>  Soaked in Piranha sol. ($H_2O_2$:$H_2 SO_4$ = 1:3) 5h<br>  Rinsed with Acetone<br>SAM modification<br>  Soaked in SAM sol. (400 μL/500 μL tube) 24h at 25° C.<br>  20 μM DSH-SAM in Acetone<br>  Washed by Acetone & 50 mM PPB (pH 7.5)<br>Enzyme modification<br>  Soaked in Complex solution (300 μL/500 μL tube)<br>  50 mM PPB (pH 7.5) 20h at 4° C.<br>  IgG-GDH 0.03 mg/mL<br>  GDH 0.015 mg/mL<br>Electrochemical Measurement |

It was investigated whether direct electron transfer from the cytochrome c-containing subunit of GDH to the electrode occurred by a glucose oxidation reaction of GDH in the IgG-GDH complex by adding glucose to react in a solution not containing a mediator using the obtained electrode with the immobilized IgG-GDH complex.

The experimental procedure is as follows.

TABLE 2

Figure 3:
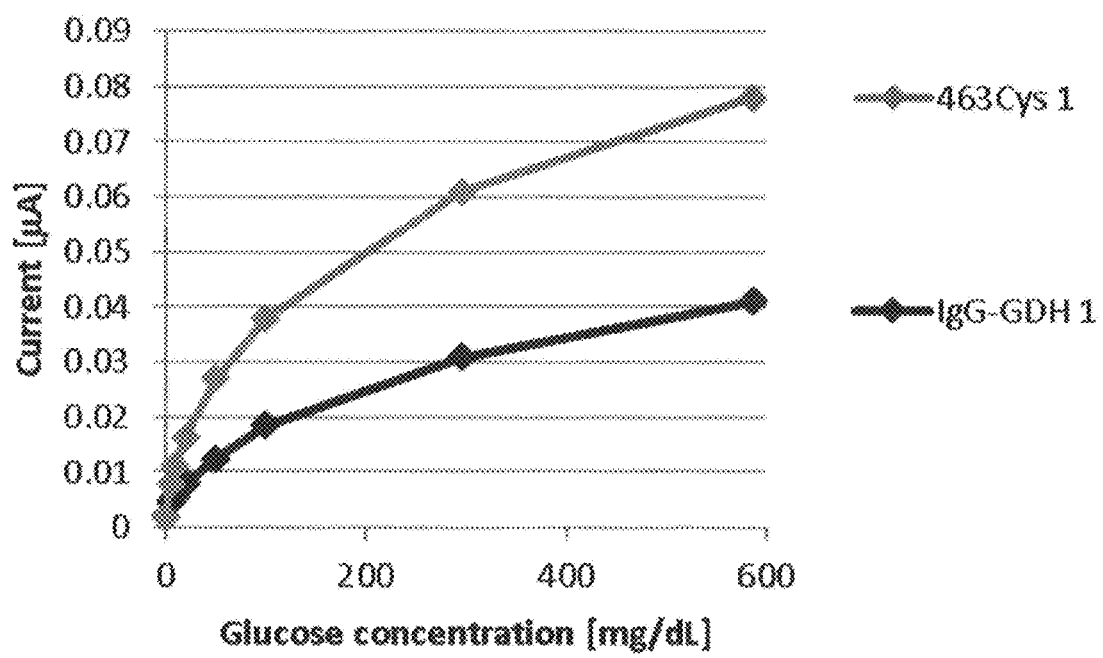
FIG. 3 shows the measurement result of glucose oxidation current in a sensor comprising an IgG-GDH immobilized electrode.

Electrochemical Measurement
Electrode chips: DEP-chip (EP-P)
Uniscan multi-channel PG580RM
3-Electrode configuration;
  WE: Enzyme modified Au wire
  CE: Pt wire
  RE: Ag/AgCl (BAS RE-1B)
Cell volume: 2 mL
Test solution: PBS
Temperature: 25 ± 1° C.
Chronoamperometry: +200 mV vs. Ag/AgCl
Measurement (1-1) Sample: 0~600 mg/dL Glucose
Measurement (1-2) Sample: 300 mg/dL Glucose + 0~10 mg/dL CRP
Measurement (2-1) Sample: 0~600 mg/dL Glucose
Measurement (2-2) Sample: 10 mg/dL CRP + 0~600 mg/dL Glucose The results are shown in FIG. 3.

The IgG-GDH immobilized electrode exhibited the same level of glucose concentration-dependent oxidation current compared with an electrode with an immobilized unlabeled GDH (463 Cys) as the control.

This suggests that the IgG-GDH complex recruited into the vicinity of the electrode can transfer the electrons generated by the catalytic activity of GDH to the electrode.

Example 2

As the GDH including a cytochrome c-containing subunit, a wild-type GDH derived from *B. cepacia* was used. Using the plasmid pTrc99Aγαβ for expressing GDH described in Japanese Patent Laid-Open No. 2012-090563, a wild-type GDH was expressed and used for the following experiment.

An SH group of a half antibody (hereinafter referred to as "rIgG") obtained by a reduction treatment of an antihuman CRP monoclonal antibody (mouse CRP-MCA (Oriental Yeast Co., Ltd.)) and an amino group included in each subunit protein of the above wild-type GDH were crosslinked with a cross-linker GMBS (Dojindo Molecular Technologies, Inc.) to prepare a CRP half antibody/GDH complex (rIgG-GDH).

Figure 4A:
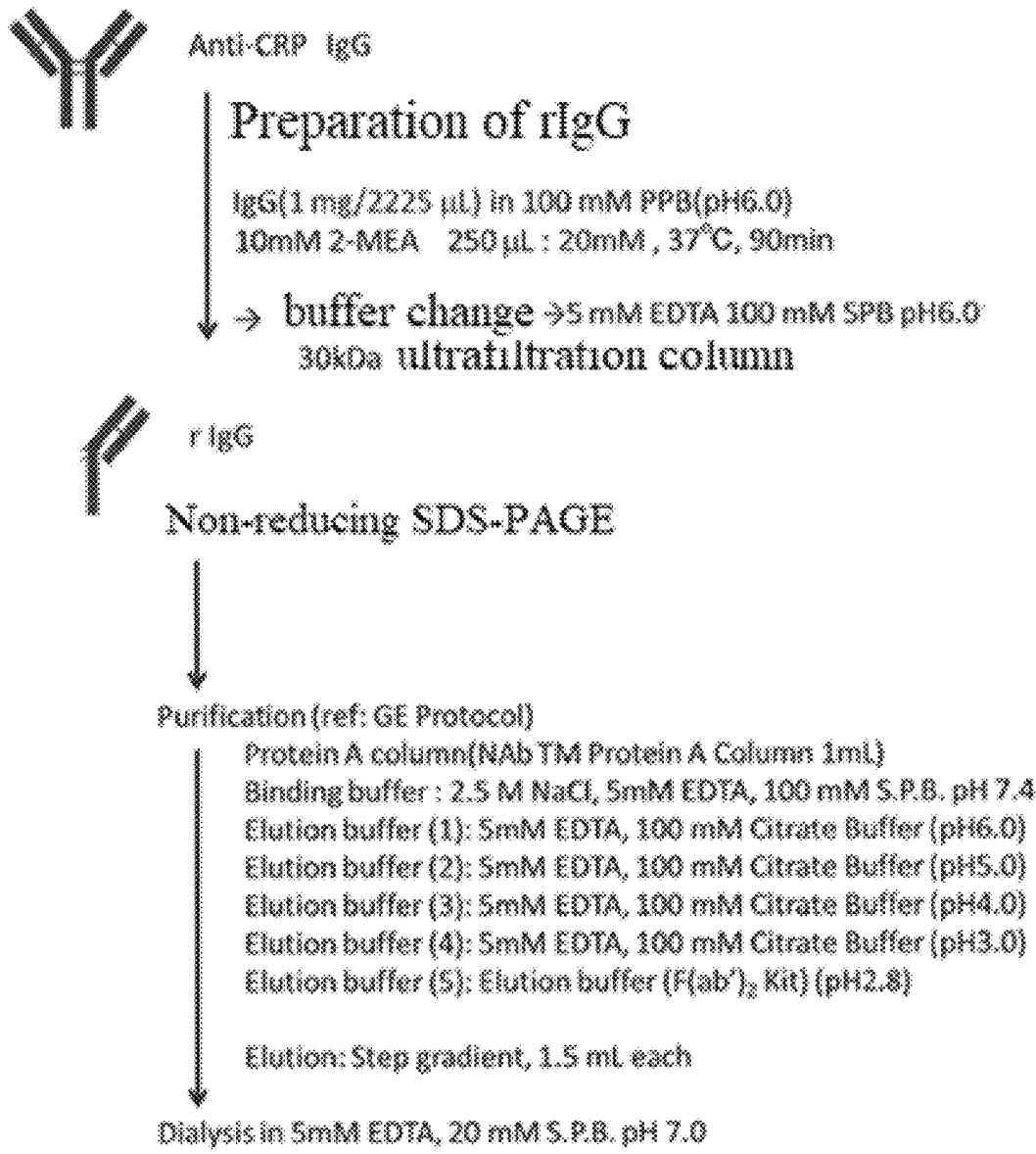
FIG. 4A shows a preparation procedure of an anti-CRP half antibody (rIgG).
Figure 4B:
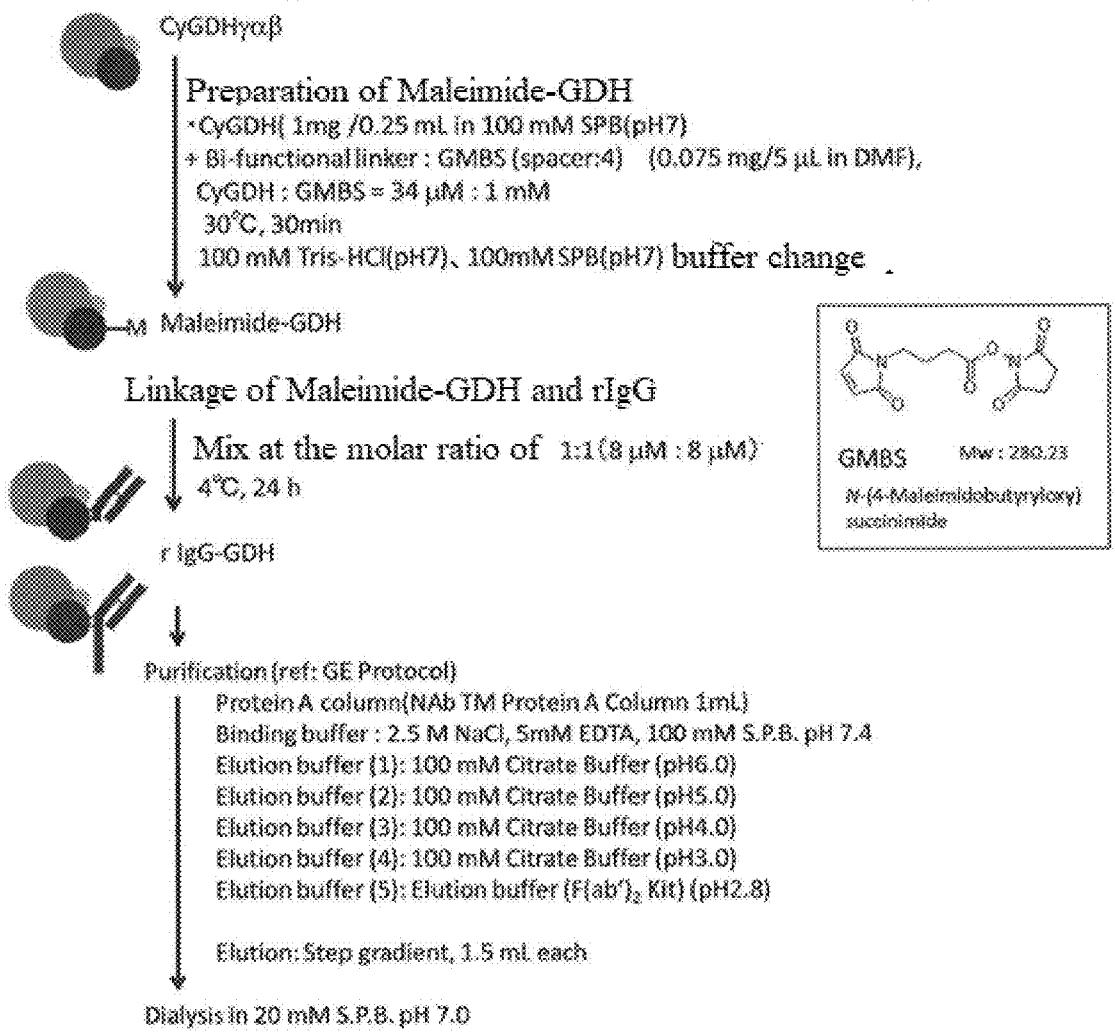
FIG. 4B shows a cross-linking procedure of an anti-CRP half antibody and GDH.

The preparation procedure of the half antibody is shown in FIG. 4A, and the preparation procedure of the half antibody/GDH complex is shown in FIG. 4B, respectively.

Figure 5:
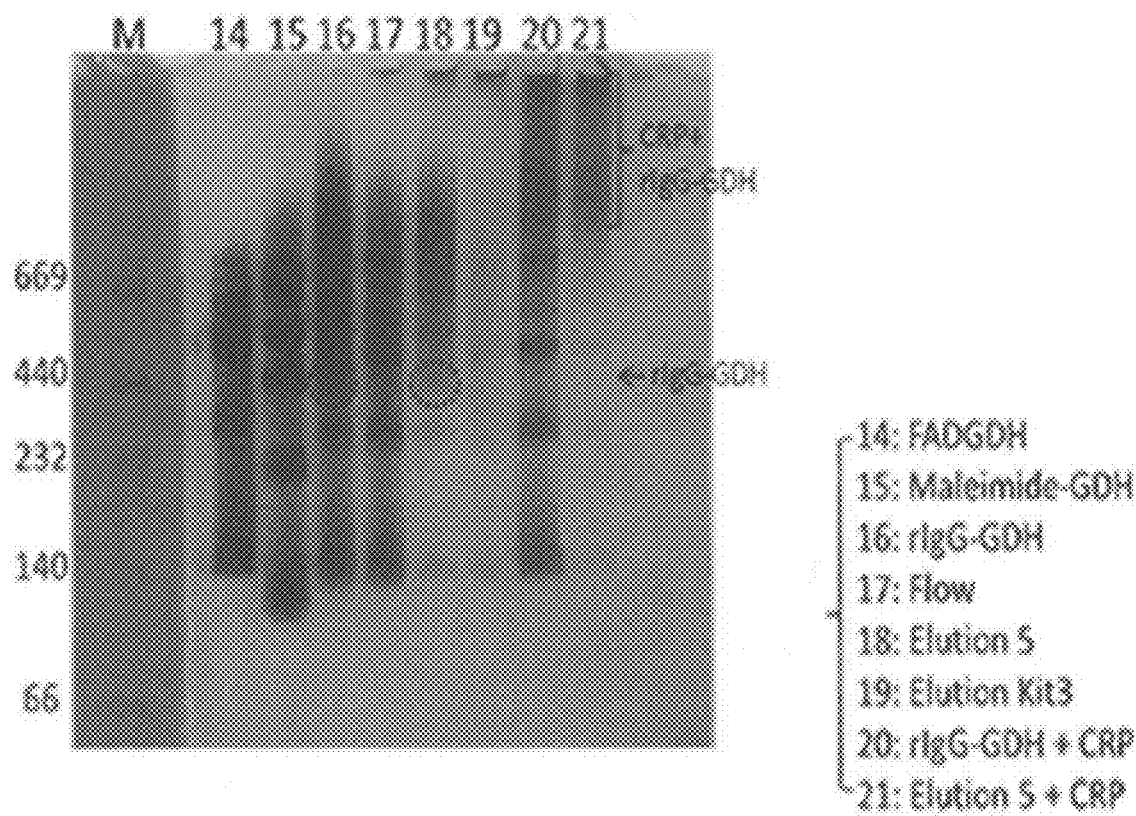
FIG. 5 shows the result of polyacrylamide gel electrophoresis and activity staining for confirming the interaction between rIgG-GDH and CRP (photograph).

The CRP binding ability of the obtained rIgG-GDH complex was examined by polyacrylamide gel electrophoresis and activity staining. The results are shown in FIG. 5. Comparing lane 18 (without CRP) and lane 21 (with CRP addition), the band near 800 kDa of lane 18 became thinner. This is conceivably because the molecular weight of the rIgG-GDH complex was shifted to the higher molecular weight site due to binding of CRP to the half antibody, which indicated that the rIgG-GDH complex was able to bind CRP.

The affinity of rIgG-GDH for CRP was examined using a protein-protein interaction analyzer BLItz from ForteBio. As a result, as shown in the table, it was confirmed that rIgG-GDH had the same affinity for CRP as CRP-MCA.

TABLE 3

|  | KD (M) | ka (1/Ms) | kd (1/sec) |
| --- | --- | --- | --- |
| CRP-MCA | 1.33.E−08 | 2.06.E+05 | 2.74.E−03 |
| rIgG-GDH | 1.08.E−08 | 5.23.E+04 | 5.67.E−04 |

Next, the above rIgG-GDH complex was immobilized on a printed carbon electrode (DEP Chip), the surface of which was modified with the SAM-forming molecule of 1-pyrenebutyric acid N-hydroxysuccinimide ester (PyNHS).

The procedure was as follows.

TABLE 4

| Sensor strip used for measurement | DEP-chip |
| --- | --- |
| Preparation of sensor | MWNT : 2% 0.4 μl × 2<br>20 min in McDry<br>+ 10 mM PyNHS 0.5 μl (in DMF)<br>20 min in McDry (remove DMF)<br>+ rIgG-GDH(Elution5), or CyGDH + rIgG(1:1)<br>2 mg/ml (50 mM TAPS pH 8.3) 2 μl<br>2 h in 25° C. under High RH<br>Store at Low Humidity (1% RH) until use |

It was investigated whether direct electron transfer from the cytochrome c-containing subunit of GDH to the electrode occurred by a glucose oxidation reaction of GDH in the rIgG-GDH complex by adding glucose to react in a solution not containing a mediator using the obtained electrode with the immobilized rIgG-GDH complex.

As the control, a sensor, in which a mixed solution of equal amounts of rIgG and GDH (non-complex) was cast, was prepared and used. Each experiment was performed twice (n=2).

The experimental procedure was as follows.

TABLE 5

Figure 6:
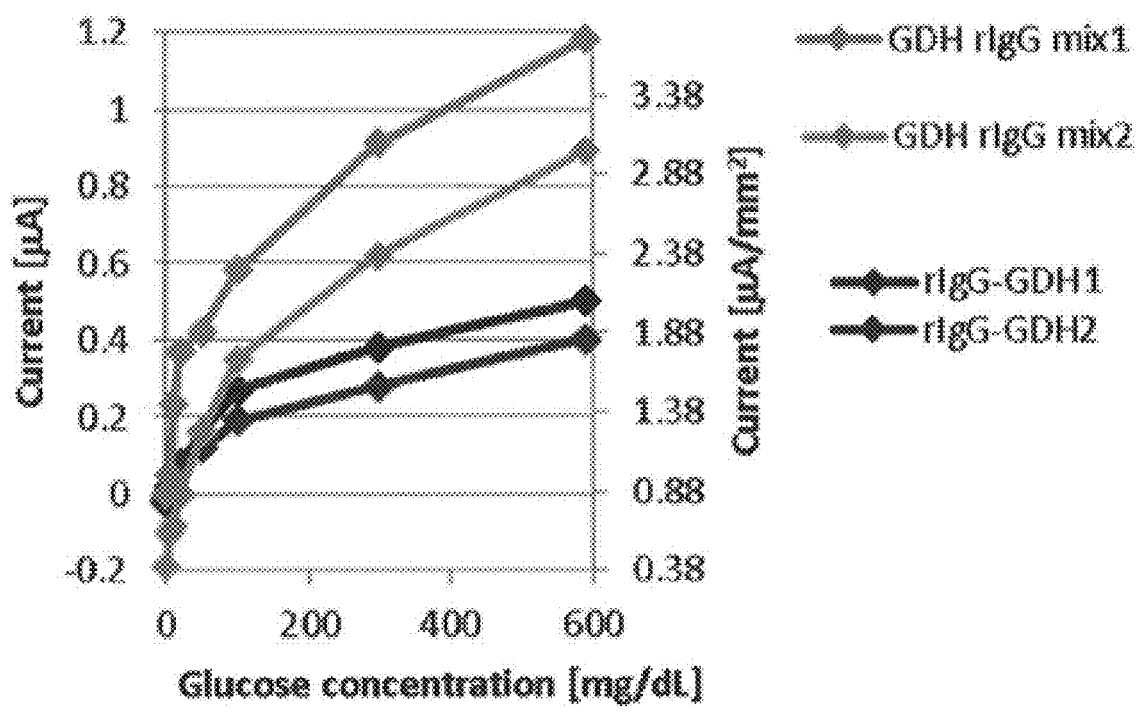
FIG. 6 shows the measurement result of a glucose oxidation current in a sensor comprising a rIgG-GDH immobilized electrode.

Electrochemical Measurement
Electrode chips: DEP-chip (EP-P)
Uniscan multi-channel PG580RM
3-Electrode configuration;
   WE: Enzyme modified carbon (2.64 mm²)
   CE: carbon (DEP-chip)
   RE: Ag/AgCl (DEP-chip)
Cell volume: 2 mL
Test solution: PBS
Temperature: 25 ± 1° C.
Chronoamperometry: + 200 mV vs. Ag/AgCl TABLE 5-continued Measurement (1-1)   Sample: 0~600 mg/dL Glucose
Measurement (1-2) Sample: 300 mg/dL Glucose + 0~10 mg/dL CRP
Measurement (2-1) Sample: 0~600 mg/dL Glucose
Measurement (2-2) Sample: 10 mg/dL CRP + 0~600 mg/dL Glucose The results are shown in FIG. 6.

The rIgG-GDH immobilized electrode exhibited a glucose concentration-dependent oxidation current, although the current value was lower than that of an electrode on which rIgG and GDH were immobilized without cross-linking. This suggests that the rIgG-GDH complex recruited into the vicinity of the electrode can transfer electrons generated by the catalytic activity of GDH to the electrode.

Example 3

Figure 7:
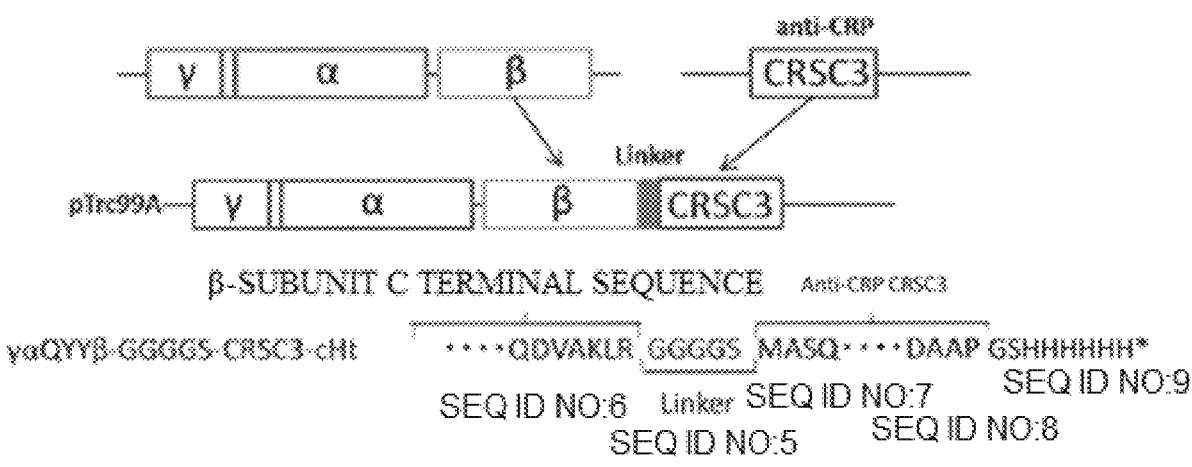
FIG. 7 shows a preparation procedure of a fusion protein (GDH-scFv(GGGGS)) of an anti-CRP single-chain antibody and GDH.

A fusion protein (GDH-scFv) in which scFv (CRSC3) having affinity to human CRP is fused to the C-terminal of the electron-transferring subunit (β subunit) of a wild-type GDH derived from *B. cepacia* was prepared. The preparation procedure of the GDH-scFv fusion protein is shown in FIG. 7. The β subunit of GDH and the scFv are linked by a GGGGS linker (SEQ ID NO: 5), and the GDH-scFv fusion protein is denoted as GDH-scFv (GGGGS).

Figure 8:
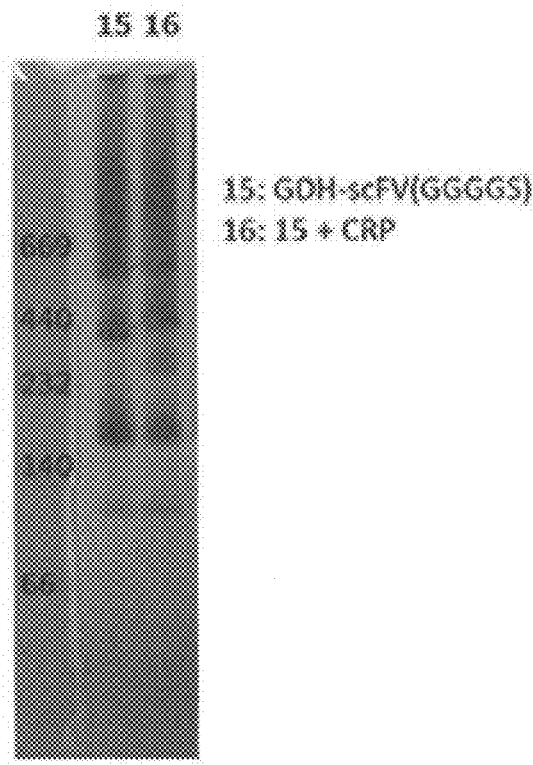
FIG. 8 shows the result of polyacrylamide gel electrophoresis and activity staining for confirming the interaction between GDH-scFv(GGGGS) and CRP.

The CRP binding ability of the obtained GDH-scFv (GGGGS) was examined by polyacrylamide gel electrophoresis and activity staining. The results are shown in FIG. 8. Comparing lane 15 (without CRP) and lane 16 (with CRP addition), the bands of lane 16 for GDH-scFv moved to a higher molecular weight site by about +100 kDa (presence of multiple bands was conceivably due to formation of a multimer). This is conceivably because the molecular weight of the GDH-scFv (GGGGS) was shifted to the higher molecular weight site due to binding of CRP to scFv, which indicated that the GDH-scFv fusion protein was able to bind CRP.

Next, the above GDH-scFv (GGGGS) was immobilized on a carbon electrode (SPCE), the surface of which was modified with the SAM-forming molecule of 1-pyrenebutyric acid N-hydroxysuccinimide ester (PyNHS).

The procedure was as follows.

TABLE 6

| Carbon electrode (SPCE) | |
| --- | --- |
| 2 % MWNT<br>SPCE: Spotted on CE (4.8 mm²)<br>1.2 μL<br>Dried out<br>1.0 μL of 10 mM PyNHS was spotted<br>Dried out<br>3 μL of 0.5 mg/mL γαβ<br>+ CRP(0, 0.05, 0.25, 1 mg/mL)<br>or 3 μL of 0.6 mg/mL GDH-scFv(GGGGS)<br>+ CRP(0, 0.05, 0.25, 1 mg/mL)<br>or 3 μL of 0.6 mg/mL GDH-scFv(GGGGS)<br>+ BSA(0, 0.05, 0.25, 1 mg/mL)<br>spotted<br>50 mM PPB (pH 7.5)<br>2 h at 25° C. (high RH)<br>Dried out<br>GA vapor, 30 min at 25° C.<br>Store at Low Humidity (1% RH) until use | *MWNT (MW-I,<br>MEIJO NANO<br>CARBON CO., LTD.)<br><br>*PyNHS in DMF<br><br><br><br><br><br><br><br><br>* CRP is a sample subjected<br>to buffer change with PPB |

It was investigated whether direct electron transfer from the cytochrome c-containing subunit of GDH to the electrode occurred by a glucose oxidation reaction of GDH in the GDH-scFv (GGGGS) by adding glucose and CRP (0, 0.1, 0.5, or 2 mg/ml) to react in a solution not containing a mediator using the obtained electrode with the immobilized GDH-scFv (GGGGS).

The experimental procedure was as follows.

TABLE 7

3-Electrode configuration; SPCE
  WE: Enzyme modified carbon
  CE: Pt wire
  RE: Ag/AgCl (BAS RE-1B)
Cell volume: 2.0 mL
Temperature: 25 ± 1° C.
Equilibration (wash): 20 min in 50 mM Tris buffer
Stirring: ) rpm
Chronoamperometry:
  Potential: +400 mV vs. Ag/AgCl
  Duration: 5 min/1 conc.
  Stirring: 300 rpm
  Test sol.: 100 mM P.P.B. (pH 7.0)

Figure 9:
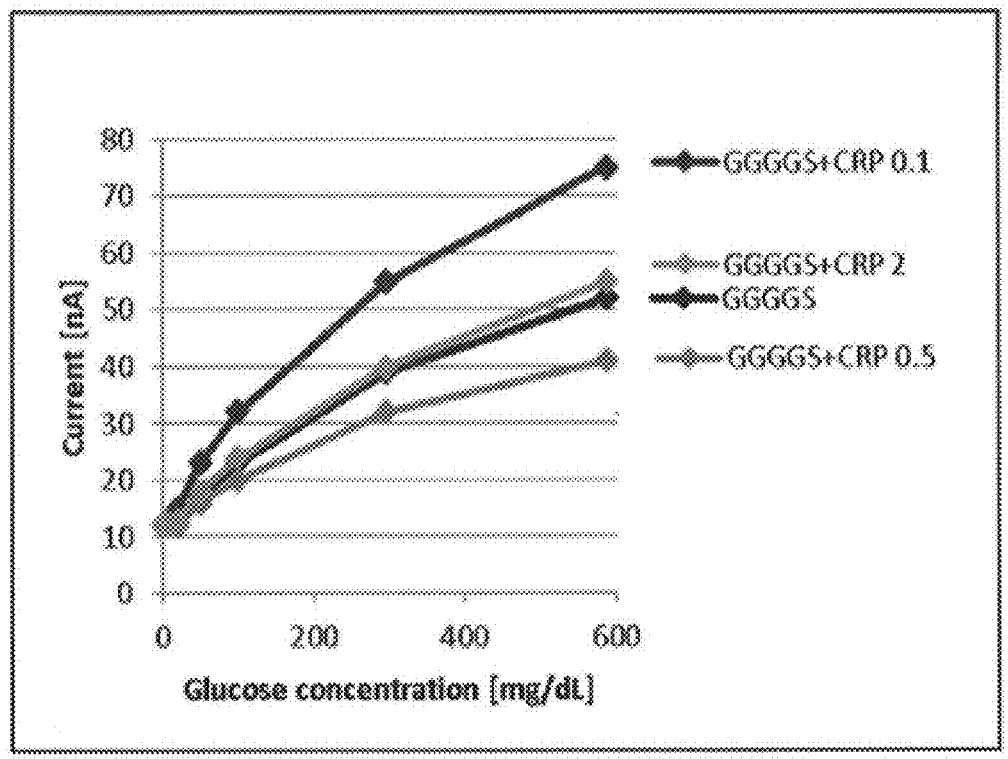
FIG. 9 shows the measurement result of a glucose oxidation current in a sensor comprising a GDH-scFv(GGGGS) immobilized electrode.

The results are shown in FIG. 9.

The GDH-scFv (GGGGS) immobilized electrode exhibited a glucose concentration-dependent oxidation current. This suggests that GDH-scFv (GGGGS) recruited into the vicinity of the electrode can transfer electrons generated by the catalytic activity of GDH to the electrode. However, a CRP concentration-dependence was not exhibited.

While the invention has been described in detail with reference to preferred embodiments thereof, it will be apparent to one skilled in the art that various changes can be made, and equivalents employed, without departing from the scope of the invention. Each of the aforementioned documents as well as JP 2018-188675 is incorporated by reference herein in its entirety.

What is claimed is:

1. A molecular recognition element comprising
   (i) a target molecule-recognizing portion, wherein the target molecule is an antigen and the target molecule-recognizing portion is an antibody against the antigen, and
   (ii) a direct electron transfer-type oxidoreductase linked to the target molecule-recognizing portion, wherein the oxidoreductase is a glucose dehydrogenase comprising a cytochrome-containing subunit of SEQ ID NO: 4.

2. The molecular recognition element according to claim 1, wherein the target molecule-recognizing portion and the direct electron transfer-type oxidoreductase are linked by a cross-linker.

3. The molecular recognition element according to claim 1, wherein the molecular recognition element comprises a fusion protein of the target molecule-recognizing portion and the direct electron transfer-type oxidoreductase.

4. The molecular recognition element according to claim 1, wherein the glucose dehydrogenase further comprises a catalytic subunit and a regulatory submit.

5. A sensor comprising an electrode, and the molecular recognition element according to claim 1, immobilized on the electrode.

6. The sensor according to claim 5, wherein the molecular recognition element is immobilized on the electrode by means of a monolayer forming molecule.

7. A method for measuring a target molecule comprising introducing a sample containing a target molecule into the sensor according to claim 5; and detecting a signal based on the target molecule.

8. A reagent for measuring a target molecule comprising the molecular recognition element according to claim 1.

* * * * *

SEQUENCE LISTING

<160> NUMBER OF SEQ ID NOS: 9

<210> SEQ ID NO 1
<211> LENGTH: 3706
<212> TYPE: DNA
<213> ORGANISM: Burkholderia cepacia
<220> FEATURE:
<221> NAME/KEY: CDS
<222> LOCATION: (258)..(761)
<220> FEATURE:
<221> NAME/KEY: CDS
<222> LOCATION: (764)..(2380)
<220> FEATURE:
<221> NAME/KEY: CDS
<222> LOCATION: (2386)..(3660)

<400> SEQUENCE: 1

```
aagctttctg tttgattgca cgcgattcta accgagcgtc tgtgaggcgg aacgcgacat      60
gcttcgtgtc gcacacgtgt cgcgccgacg acacaaaaat gcagcgaaat ggctgatcgt     120
tacgaatggc tgacacattg aatggactat aaaaccattg tccgttccgg aatgtgcgcg     180
tacatttcag gtccgcgccg atttttgaga aatatcaagc gtggttttcc cgaatccggt     240
gttcgagaga aggaaac atg cac aac gac aac act ccc cac tcg cgt cgc         290
               Met His Asn Asp Asn Thr Pro His Ser Arg Arg
                 1               5                  10 cac ggc gac gca gcc gca tca ggc atc acg cgg cgt caa tgg ttg caa        338
His Gly Asp Ala Ala Ala Ser Gly Ile Thr Arg Arg Gln Trp Leu Gln
            15                  20                  25 ggc gcg ctg gcg ctg acc gca gcg ggc ctc acg ggt tcg ctg aca ttg        386
Gly Ala Leu Ala Leu Thr Ala Ala Gly Leu Thr Gly Ser Leu Thr Leu
        30                  35                  40 cgg gcg ctt gca gac aac ccc ggc act gcg ccg ctc gat acg ttc atg        434
Arg Ala Leu Ala Asp Asn Pro Gly Thr Ala Pro Leu Asp Thr Phe Met
    45                  50                  55 acg ctt tcc gaa tcg ctg acc ggc aag aaa ggg ctc agc cgc gtg atc        482
Thr Leu Ser Glu Ser Leu Thr Gly Lys Lys Gly Leu Ser Arg Val Ile
60                  65                  70                  75 ggc gag cgc ctg ctg cag gcg ctg cag aag ggc tcg ttc aag acg gcc        530
Gly Glu Arg Leu Leu Gln Ala Leu Gln Lys Gly Ser Phe Lys Thr Ala
                80                  85                  90 gac agc ctg ccg cag ctc gcc ggc gcg ctc gcg tcc ggt tcg ctg acg        578
Asp Ser Leu Pro Gln Leu Ala Gly Ala Leu Ala Ser Gly Ser Leu Thr
            95                 100                 105 cct gaa cag gaa tcg ctc gca ctg acg atc ctc gag gcc tgg tat ctc        626
Pro Glu Gln Glu Ser Leu Ala Leu Thr Ile Leu Glu Ala Trp Tyr Leu
        110                 115                 120
```

-continued

| | | |
|---|---|---|
| ggc atc gtc gac aac gtc gtg att acg tac gag gaa gca tta atg ttc<br>Gly Ile Val Asp Asn Val Val Ile Thr Tyr Glu Glu Ala Leu Met Phe<br>125              130              135 | 674 |
| ggc gtc gtg tcc gat acg ctc gtg atc cgt tcg tat tgc ccc aac aaa<br>Gly Val Val Ser Asp Thr Leu Val Ile Arg Ser Tyr Cys Pro Asn Lys<br>140              145              150              155 | 722 |
| ccc ggc ttc tgg gcc gac aaa ccg atc gag agg caa gcc tg atg gcc<br>Pro Gly Phe Trp Ala Asp Lys Pro Ile Glu Arg Gln Ala    Met Ala<br>160              165                   170 | 769 |
| gat acc gat acg caa aag gcc gac gtc gtc gtt gga tcg ggt gtc<br>Asp Thr Asp Thr Gln Lys Ala Asp Val Val Val Gly Ser Gly Val<br>175              180              185 | 817 |
| gcg ggc gcg atc gtc gcg cat cag ctc gcg atg gcg ggc aag gcg gtg<br>Ala Gly Ala Ile Val Ala His Gln Leu Ala Met Ala Gly Lys Ala Val<br>190              195              200 | 865 |
| atc ctg ctc gaa gcg ggc ccg cgc atg ccg cgc tgg gaa atc gtc gag<br>Ile Leu Leu Glu Ala Gly Pro Arg Met Pro Arg Trp Glu Ile Val Glu<br>205              210              215 | 913 |
| cgc ttc cgc aat cag ccc gac aag atg gac ttc atg gcg ccg tac ccg<br>Arg Phe Arg Asn Gln Pro Asp Lys Met Asp Phe Met Ala Pro Tyr Pro<br>220              225              230 | 961 |
| tcg agc ccc tgg gcg ccg cat ccc gag tac ggc ccg ccg aac gac tac<br>Ser Ser Pro Trp Ala Pro His Pro Glu Tyr Gly Pro Pro Asn Asp Tyr<br>235              240              245              250 | 1009 |
| ctg atc ctg aag ggc gag cac aag ttc aac tcg cag tac atc cgc gcg<br>Leu Ile Leu Lys Gly Glu His Lys Phe Asn Ser Gln Tyr Ile Arg Ala<br>255              260              265 | 1057 |
| gtg ggc ggc acg acg tgg cac tgg gcc gcg tcg gcg tgg cgc ttc att<br>Val Gly Gly Thr Thr Trp His Trp Ala Ala Ser Ala Trp Arg Phe Ile<br>270              275              280 | 1105 |
| ccg aac gac ttc aag atg aag agc gtg tac ggc gtc ggc cgc gac tgg<br>Pro Asn Asp Phe Lys Met Lys Ser Val Tyr Gly Val Gly Arg Asp Trp<br>285              290              295 | 1153 |
| ccg atc cag tac gac gat ctc gag ccg tac tat cag cgc gcg gag gaa<br>Pro Ile Gln Tyr Asp Asp Leu Glu Pro Tyr Tyr Gln Arg Ala Glu Glu<br>300              305              310 | 1201 |
| gag ctc ggc gtg tgg ggc ccg ggc ccc gag gaa gat ctg tac tcg ccg<br>Glu Leu Gly Val Trp Gly Pro Gly Pro Glu Glu Asp Leu Tyr Ser Pro<br>315              320              325              330 | 1249 |
| cgc aag cag ccg tat ccg atg ccg ccg ctg ccg ttg tcg ttc aac gag<br>Arg Lys Gln Pro Tyr Pro Met Pro Pro Leu Pro Leu Ser Phe Asn Glu<br>335              340              345 | 1297 |
| cag acc atc aag acg gcg ctg aac aac tac gat ccg aag ttc cat gtc<br>Gln Thr Ile Lys Thr Ala Leu Asn Asn Tyr Asp Pro Lys Phe His Val<br>350              355              360 | 1345 |
| gtg acc gag ccg gtc gcg cgc aac agc cgc ccg tac gac ggc cgc ccg<br>Val Thr Glu Pro Val Ala Arg Asn Ser Arg Pro Tyr Asp Gly Arg Pro<br>365              370              375 | 1393 |
| act tgt tgc ggc aac aac aac tgc atg ccg atc tgc ccg atc ggc gcg<br>Thr Cys Cys Gly Asn Asn Asn Cys Met Pro Ile Cys Pro Ile Gly Ala<br>380              385              390 | 1441 |
| atg tac aac ggc atc gtg cac gtc gag aag gcc gaa cgc gcc ggc gcg<br>Met Tyr Asn Gly Ile Val His Val Glu Lys Ala Glu Arg Ala Gly Ala<br>395              400              405              410 | 1489 |
| aag ctg atc gag aac gcg gtc gtc tac aag ctc gag acg ggc ccg gac<br>Lys Leu Ile Glu Asn Ala Val Val Tyr Lys Leu Glu Thr Gly Pro Asp<br>415              420              425 | 1537 |
| aag cgc atc gtc gcg gcg ctc tac aag gac aag acg ggc gcc gag cat<br>Lys Arg Ile Val Ala Ala Leu Tyr Lys Asp Lys Thr Gly Ala Glu His<br>430              435              440 | 1585 |

-continued

| | |
|---|---|
| cgc gtc gaa ggc aag tat ttc gtg ctc gcc gcg aac ggc atc gag acg<br>Arg Val Glu Gly Lys Tyr Phe Val Leu Ala Ala Asn Gly Ile Glu Thr<br>     445                     450                455 | 1633 |
| ccg aag atc ctg ctg atg tcc gcg aac cgc gat ttc ccg aac ggt gtc<br>Pro Lys Ile Leu Leu Met Ser Ala Asn Arg Asp Phe Pro Asn Gly Val<br>460                   465                   470 | 1681 |
| gcg aac agc tcg gac atg gtc ggc cgc aac ctg atg gac cat ccg ggc<br>Ala Asn Ser Ser Asp Met Val Gly Arg Asn Leu Met Asp His Pro Gly<br>475                   480               485                490 | 1729 |
| acc ggc gtg tcg ttc tat gcg agc gag aag ctg tgg ccg ggc cgc ggc<br>Thr Gly Val Ser Phe Tyr Ala Ser Glu Lys Leu Trp Pro Gly Arg Gly<br>                   495                 500                505 | 1777 |
| ccg cag gag atg acg tcg ctg atc ggt ttc cgc gac ggt ccg ttc cgc<br>Pro Gln Glu Met Thr Ser Leu Ile Gly Phe Arg Asp Gly Pro Phe Arg<br>510                   515                   520 | 1825 |
| gcg acc gaa gcg gcg aag aag atc cac ctg tcg aac ctg tcg cgc atc<br>Ala Thr Glu Ala Ala Lys Lys Ile His Leu Ser Asn Leu Ser Arg Ile<br>         525                   530                535 | 1873 |
| gac cag gag acg cag aag atc ttc aag gcc ggc aag ctg atg aag ccc<br>Asp Gln Glu Thr Gln Lys Ile Phe Lys Ala Gly Lys Leu Met Lys Pro<br>540                   545                   550 | 1921 |
| gac gag ctc gac gcg cag atc cgc gac cgt tcc gca cgc tac gtg cag<br>Asp Glu Leu Asp Ala Gln Ile Arg Asp Arg Ser Ala Arg Tyr Val Gln<br>555                   560                   565                570 | 1969 |
| ttc gac tgc ttc cac gaa atc ctg ccg caa ccc gag aac cgc atc gtg<br>Phe Asp Cys Phe His Glu Ile Leu Pro Gln Pro Glu Asn Arg Ile Val<br>                   575                   580                585 | 2017 |
| ccg agc aag acg gcg acc gat gcg atc ggc att ccg cgc ccc gag atc<br>Pro Ser Lys Thr Ala Thr Asp Ala Ile Gly Ile Pro Arg Pro Glu Ile<br>590                   595                   600 | 2065 |
| acg tat gcg atc gac gac tac gtg aag cgc ggc gcc gcg cat acg cgc<br>Thr Tyr Ala Ile Asp Asp Tyr Val Lys Arg Gly Ala Ala His Thr Arg<br>         605                   610                615 | 2113 |
| gag gtc tac gcg acc gcc gcg aag gtg ctc ggc ggc acg gac gtc gtg<br>Glu Val Tyr Ala Thr Ala Ala Lys Val Leu Gly Gly Thr Asp Val Val<br>620                   625                   630 | 2161 |
| ttc aac gac gaa ttc gcg ccg aac aat cac atc acg ggc tcg acg atc<br>Phe Asn Asp Glu Phe Ala Pro Asn Asn His Ile Thr Gly Ser Thr Ile<br>635                   640                   645                650 | 2209 |
| atg ggc gcc gat gcg cgc gac tcc gtc gtc gac aag gac tgc cgc acg<br>Met Gly Ala Asp Ala Arg Asp Ser Val Val Asp Lys Asp Cys Arg Thr<br>                   655                   660                665 | 2257 |
| ttc gac cat ccg aac ctg ttc att tcg agc agc gcg acg atg ccg acc<br>Phe Asp His Pro Asn Leu Phe Ile Ser Ser Ser Ala Thr Met Pro Thr<br>670                   675                   680 | 2305 |
| gtc ggt acc gta aac gtg acg ctg acg atc gcc gcg ctc gcg ctg cgg<br>Val Gly Thr Val Asn Val Thr Leu Thr Ile Ala Ala Leu Ala Leu Arg<br>         685                   690                695 | 2353 |
| atg tcg gac acg ctg aag aag gaa gtc tgacc gtg cgg aaa tct act ctc<br>Met Ser Asp Thr Leu Lys Lys Glu Val     Met Arg Lys Ser Thr Leu<br>700                   705                              710 | 2403 |
| act ttc ctc atc gcc ggc tgc ctc gcg ttg ccg ggc ttc gcg cgc gcg<br>Thr Phe Leu Ile Ala Gly Cys Leu Ala Leu Pro Gly Phe Ala Arg Ala<br>715                   720                   725 | 2451 |
| gcc gat gcg gcc gat ccg gcg ctg gtc aag cgc ggc gaa tac ctc gcg<br>Ala Asp Ala Ala Asp Pro Ala Leu Val Lys Arg Gly Glu Tyr Leu Ala<br>730                   735                   740                745 | 2499 |
| acc gcc ggc gac tgc atg gcc tgc cac acc gtg aag ggc ggc aag ccg<br>Thr Ala Gly Asp Cys Met Ala Cys His Thr Val Lys Gly Gly Lys Pro<br>                   750                   755                760 | 2547 |

-continued

| | | |
|---|---|---|
| tac gcg ggc ggc ctt ggc atg ccg gta ccg atg ctc ggc aag atc tac<br>Tyr Ala Gly Gly Leu Gly Met Pro Val Pro Met Leu Gly Lys Ile Tyr<br>             765                         770                     775 | 2595 | |
| acg agc aac atc acg ccc gat ccc gat acg ggc atc ggc aaa tgg acg<br>Thr Ser Asn Ile Thr Pro Asp Pro Asp Thr Gly Ile Gly Lys Trp Thr<br>        780                    785                     790 | 2643 | |
| ttc gag gac ttc gag cgc gcg gtg cgg cac ggc gtg tcg aag aac ggc<br>Phe Glu Asp Phe Glu Arg Ala Val Arg His Gly Val Ser Lys Asn Gly<br>     795                    800                     805 | 2691 | |
| gac aac ctg tat ccg gcg atg ccg tac gtg tcg tac gcg aag atc acg<br>Asp Asn Leu Tyr Pro Ala Met Pro Tyr Val Ser Tyr Ala Lys Ile Thr<br>810                     815                     820                825 | 2739 | |
| gac gac gac gta cgc gcg ctg tac gcc tac ttc atg cac ggc gtc gag<br>Asp Asp Asp Val Arg Ala Leu Tyr Ala Tyr Phe Met His Gly Val Glu<br>             830                         835                     840 | 2787 | |
| ccg gtc aag cag gcg ccg ccg aag aac gag att ccc gcg ctg ctc agc<br>Pro Val Lys Gln Ala Pro Pro Lys Asn Glu Ile Pro Ala Leu Leu Ser<br>        845                    850                     855 | 2835 | |
| atg cgc tgg ccg ctg aag atc tgg aac tgg ctg ttc ctg aag gac ggc<br>Met Arg Trp Pro Leu Lys Ile Trp Asn Trp Leu Phe Leu Lys Asp Gly<br>             860                         865                     870 | 2883 | |
| ccg tac cag ccg aag ccg tcg cag agc gcc gaa tgg aat cgc ggc gcg<br>Pro Tyr Gln Pro Lys Pro Ser Gln Ser Ala Glu Trp Asn Arg Gly Ala<br>     875                    880                     885 | 2931 | |
| tat ctg gtg cag ggt ctc gcg cac tgc agc acg tgc cac acg ccg cgc<br>Tyr Leu Val Gln Gly Leu Ala His Cys Ser Thr Cys His Thr Pro Arg<br>890                   895                     900                905 | 2979 | |
| ggc atc gcg atg cag gag aag tcg ctc gac gaa acc ggc ggc agc ttc<br>Gly Ile Ala Met Gln Glu Lys Ser Leu Asp Glu Thr Gly Gly Ser Phe<br>             910                         915                     920 | 3027 | |
| ctc gcg ggg tcg gtg ctc gcc ggc tgg gac ggc tac aac atc acg tcg<br>Leu Ala Gly Ser Val Leu Ala Gly Trp Asp Gly Tyr Asn Ile Thr Ser<br>        925                    930                     935 | 3075 | |
| gac ccg aat gcg ggg atc ggc agc tgg acg cag cag cag ctc gtg cag<br>Asp Pro Asn Ala Gly Ile Gly Ser Trp Thr Gln Gln Gln Leu Val Gln<br>             940                         945                     950 | 3123 | |
| tat ttg cgc acc ggc agc gtg ccg ggc gtc gcg cag gcg gcc ggg ccg<br>Tyr Leu Arg Thr Gly Ser Val Pro Gly Val Ala Gln Ala Ala Gly Pro<br>     955                    960                     965 | 3171 | |
| atg gcc gag gcg gtc gag cac agc ttc tcg aag atg acc gaa gcg gac<br>Met Ala Glu Ala Val Glu His Ser Phe Ser Lys Met Thr Glu Ala Asp<br>970                     975                     980                985 | 3219 | |
| atc ggt gcg atc gcc acg tac gtc cgc acg gtg ccg gcc gtt gcc gac<br>Ile Gly Ala Ile Ala Thr Tyr Val Arg Thr Val Pro Ala Val Ala Asp<br>             990                         995                   1000 | 3267 | |
| agc aac gcg aag cag ccg cgg tcg tcg tgg ggc aag ccg gcc gag<br>Ser Asn Ala Lys Gln Pro Arg Ser Ser Trp Gly Lys Pro Ala Glu<br>            1005                     1010                  1015 | 3312 | |
| gac ggg ctg aag ctg cgc ggt gtc gcg ctc gcg tcg tcg ggc atc<br>Asp Gly Leu Lys Leu Arg Gly Val Ala Leu Ala Ser Ser Gly Ile<br>            1020                     1025                  1030 | 3357 | |
| gat ccg gcg cgg ctg tat ctc ggc aac tgc gcg acg tgc cac cag<br>Asp Pro Ala Arg Leu Tyr Leu Gly Asn Cys Ala Thr Cys His Gln<br>            1035                     1040                  1045 | 3402 | |
| atg cag ggc aag ggc acg ccg gac ggc tat tac ccg tcg ctg ttc<br>Met Gln Gly Lys Gly Thr Pro Asp Gly Tyr Tyr Pro Ser Leu Phe<br>            1050                     1055                  1060 | 3447 | |
| cac aac tcc acc gtc ggc gcg tcg aat ccg tcg aac ctc gtg cag<br>His Asn Ser Thr Val Gly Ala Ser Asn Pro Ser Asn Leu Val Gln<br>            1065                     1070                  1075 | 3492 | |

-continued

| | | | | | | | | | | | | |
|---|---|---|---|---|---|---|---|---|---|---|---|---|
| gtg | atc | ctg | aac | ggc | gtg | cag | cgc | aag | atc | ggc | agc | gag | gat | atc | 3537 |
| Val | Ile | Leu | Asn | Gly | Val | Gln | Arg | Lys | Ile | Gly | Ser | Glu | Asp | Ile | |
| | | 1080 | | | | 1085 | | | | | 1090 | | | | |

| ggg | atg | ccc | gct | ttc | cgc | tac | gat | ctg | aac | gac | gcg | cag | atc | gcc | 3582 |
| Gly | Met | Pro | Ala | Phe | Arg | Tyr | Asp | Leu | Asn | Asp | Ala | Gln | Ile | Ala | |
| | 1095 | | | | | 1100 | | | | | 1105 | | | | |

| gcg | ctg | acg | aac | tac | gtg | acc | gcg | cag | ttc | ggc | aat | ccg | gcg | gcg | 3627 |
| Ala | Leu | Thr | Asn | Tyr | Val | Thr | Ala | Gln | Phe | Gly | Asn | Pro | Ala | Ala | |
| | 1110 | | | | | 1115 | | | | | 1120 | | | | |

| aag | gtg | acg | gag | cag | gac | gtc | gcg | aag | ctg | cgc | tgacatagtc | 3670 |
| Lys | Val | Thr | Glu | Gln | Asp | Val | Ala | Lys | Leu | Arg | |
| | | 1125 | | | | 1130 | | | | | | gggcgcgccg acacggcgca accgatagga caggag        3706

<210> SEQ ID NO 2
<211> LENGTH: 168
<212> TYPE: PRT
<213> ORGANISM: Burkholderia cepacia

<400> SEQUENCE: 2

Met His Asn Asp Asn Thr Pro His Ser Arg Arg His Gly Asp Ala Ala
1               5                   10                  15

Ala Ser Gly Ile Thr Arg Arg Gln Trp Leu Gln Gly Ala Leu Ala Leu
            20                  25                  30

Thr Ala Ala Gly Leu Thr Gly Ser Leu Thr Leu Arg Ala Leu Ala Asp
        35                  40                  45

Asn Pro Gly Thr Ala Pro Leu Asp Thr Phe Met Thr Leu Ser Glu Ser
    50                  55                  60

Leu Thr Gly Lys Lys Gly Leu Ser Arg Val Ile Gly Glu Arg Leu Leu
65                  70                  75                  80

Gln Ala Leu Gln Lys Gly Ser Phe Lys Thr Ala Asp Ser Leu Pro Gln
                85                  90                  95

Leu Ala Gly Ala Leu Ala Ser Gly Ser Leu Thr Pro Glu Gln Glu Ser
            100                 105                 110

Leu Ala Leu Thr Ile Leu Glu Ala Trp Tyr Leu Gly Ile Val Asp Asn
        115                 120                 125

Val Val Ile Thr Tyr Glu Glu Ala Leu Met Phe Gly Val Val Ser Asp
    130                 135                 140

Thr Leu Val Ile Arg Ser Tyr Cys Pro Asn Lys Pro Gly Phe Trp Ala
145                 150                 155                 160

Asp Lys Pro Ile Glu Arg Gln Ala
                165

<210> SEQ ID NO 3
<211> LENGTH: 539
<212> TYPE: PRT
<213> ORGANISM: Burkholderia cepacia

<400> SEQUENCE: 3

Met Ala Asp Thr Asp Thr Gln Lys Ala Asp Val Val Val Val Gly Ser
1               5                   10                  15

Gly Val Ala Gly Ala Ile Val Ala His Gln Leu Ala Met Ala Gly Lys
            20                  25                  30

Ala Val Ile Leu Leu Glu Ala Gly Pro Arg Met Pro Arg Trp Glu Ile
        35                  40                  45

Val Glu Arg Phe Arg Asn Gln Pro Asp Lys Met Asp Phe Met Ala Pro
    50                  55                  60

```
Tyr Pro Ser Ser Pro Trp Ala Pro His Pro Glu Tyr Gly Pro Pro Asn
 65                  70                  75                  80

Asp Tyr Leu Ile Leu Lys Gly Glu His Lys Phe Asn Ser Gln Tyr Ile
                 85                  90                  95

Arg Ala Val Gly Gly Thr Thr Trp His Trp Ala Ala Ser Ala Trp Arg
            100                 105                 110

Phe Ile Pro Asn Asp Phe Lys Met Lys Ser Val Tyr Gly Val Gly Arg
        115                 120                 125

Asp Trp Pro Ile Gln Tyr Asp Asp Leu Glu Pro Tyr Tyr Gln Arg Ala
    130                 135                 140

Glu Glu Glu Leu Gly Val Trp Gly Pro Gly Pro Glu Glu Asp Leu Tyr
145                 150                 155                 160

Ser Pro Arg Lys Gln Pro Tyr Pro Met Pro Pro Leu Pro Leu Ser Phe
                165                 170                 175

Asn Glu Gln Thr Ile Lys Thr Ala Leu Asn Asn Tyr Asp Pro Lys Phe
                180                 185                 190

His Val Val Thr Glu Pro Val Ala Arg Asn Ser Arg Pro Tyr Asp Gly
            195                 200                 205

Arg Pro Thr Cys Cys Gly Asn Asn Cys Met Pro Ile Cys Pro Ile
210                 215                 220

Gly Ala Met Tyr Asn Gly Ile Val His Val Glu Lys Ala Glu Arg Ala
225                 230                 235                 240

Gly Ala Lys Leu Ile Glu Asn Ala Val Val Tyr Lys Leu Glu Thr Gly
                245                 250                 255

Pro Asp Lys Arg Ile Val Ala Ala Leu Tyr Lys Asp Lys Thr Gly Ala
            260                 265                 270

Glu His Arg Val Glu Gly Lys Tyr Phe Val Leu Ala Ala Asn Gly Ile
        275                 280                 285

Glu Thr Pro Lys Ile Leu Leu Met Ser Ala Asn Arg Asp Phe Pro Asn
    290                 295                 300

Gly Val Ala Asn Ser Ser Asp Met Val Gly Arg Asn Leu Met Asp His
305                 310                 315                 320

Pro Gly Thr Gly Val Ser Phe Tyr Ala Ser Glu Lys Leu Trp Pro Gly
                325                 330                 335

Arg Gly Pro Gln Glu Met Thr Ser Leu Ile Gly Phe Arg Asp Gly Pro
            340                 345                 350

Phe Arg Ala Thr Glu Ala Ala Lys Lys Ile His Leu Ser Asn Leu Ser
        355                 360                 365

Arg Ile Asp Gln Glu Thr Gln Lys Ile Phe Lys Ala Gly Lys Leu Met
    370                 375                 380

Lys Pro Asp Glu Leu Asp Ala Gln Ile Arg Asp Arg Ser Ala Arg Tyr
385                 390                 395                 400

Val Gln Phe Asp Cys Phe His Glu Ile Leu Pro Gln Pro Glu Asn Arg
                405                 410                 415

Ile Val Pro Ser Lys Thr Ala Thr Asp Ala Ile Gly Ile Pro Arg Pro
            420                 425                 430

Glu Ile Thr Tyr Ala Ile Asp Asp Tyr Val Lys Arg Gly Ala Ala His
        435                 440                 445

Thr Arg Glu Val Tyr Ala Thr Ala Lys Val Leu Gly Gly Thr Asp
    450                 455                 460

Val Val Phe Asn Asp Glu Phe Ala Pro Asn Asn His Ile Thr Gly Ser
465                 470                 475                 480
```

```
Thr Ile Met Gly Ala Asp Ala Arg Asp Ser Val Val Asp Lys Asp Cys
                485                 490                 495

Arg Thr Phe Asp His Pro Asn Leu Phe Ile Ser Ser Ser Ala Thr Met
            500                 505                 510

Pro Thr Val Gly Thr Val Asn Val Thr Leu Thr Ile Ala Ala Leu Ala
            515                 520                 525

Leu Arg Met Ser Asp Thr Leu Lys Lys Glu Val
        530                 535

<210> SEQ ID NO 4
<211> LENGTH: 425
<212> TYPE: PRT
<213> ORGANISM: Burkholderia cepacia

<400> SEQUENCE: 4

Met Arg Lys Ser Thr Leu Thr Phe Leu Ile Ala Gly Cys Leu Ala Leu
1               5                   10                  15

Pro Gly Phe Ala Arg Ala Ala Asp Ala Ala Asp Pro Ala Leu Val Lys
            20                  25                  30

Arg Gly Glu Tyr Leu Ala Thr Ala Gly Asp Cys Met Ala Cys His Thr
        35                  40                  45

Val Lys Gly Gly Lys Pro Tyr Ala Gly Gly Leu Gly Met Pro Val Pro
50                  55                  60

Met Leu Gly Lys Ile Tyr Thr Ser Asn Ile Thr Pro Asp Pro Asp Thr
65                  70                  75                  80

Gly Ile Gly Lys Trp Thr Phe Glu Asp Phe Glu Arg Ala Val Arg His
                85                  90                  95

Gly Val Ser Lys Asn Gly Asp Asn Leu Tyr Pro Ala Met Pro Tyr Val
            100                 105                 110

Ser Tyr Ala Lys Ile Thr Asp Asp Val Arg Ala Leu Tyr Ala Tyr
        115                 120                 125

Phe Met His Gly Val Glu Pro Val Lys Gln Ala Pro Lys Asn Glu
    130                 135                 140

Ile Pro Ala Leu Leu Ser Met Arg Trp Pro Leu Lys Ile Trp Asn Trp
145                 150                 155                 160

Leu Phe Leu Lys Asp Gly Pro Tyr Gln Pro Lys Pro Ser Gln Ser Ala
                165                 170                 175

Glu Trp Asn Arg Gly Ala Tyr Leu Val Gln Gly Leu Ala His Cys Ser
            180                 185                 190

Thr Cys His Thr Pro Arg Gly Ile Ala Met Gln Glu Lys Ser Leu Asp
        195                 200                 205

Glu Thr Gly Gly Ser Phe Leu Ala Gly Ser Val Leu Ala Gly Trp Asp
    210                 215                 220

Gly Tyr Asn Ile Thr Ser Asp Pro Asn Ala Gly Ile Gly Ser Trp Thr
225                 230                 235                 240

Gln Gln Gln Leu Val Gln Tyr Leu Arg Thr Gly Ser Val Pro Gly Val
                245                 250                 255

Ala Gln Ala Ala Gly Pro Met Ala Glu Ala Val Glu His Ser Phe Ser
            260                 265                 270

Lys Met Thr Glu Ala Asp Ile Gly Ala Ile Ala Thr Tyr Val Arg Thr
        275                 280                 285

Val Pro Ala Val Ala Asp Ser Asn Ala Lys Gln Pro Arg Ser Ser Trp
    290                 295                 300

Gly Lys Pro Ala Glu Asp Gly Leu Lys Leu Arg Gly Val Ala Leu Ala
305                 310                 315                 320
```

```
Ser Ser Gly Ile Asp Pro Ala Arg Leu Tyr Leu Gly Asn Cys Ala Thr
            325                 330                 335

Cys His Gln Met Gln Gly Lys Gly Thr Pro Asp Gly Tyr Tyr Pro Ser
        340                 345                 350

Leu Phe His Asn Ser Thr Val Gly Ala Ser Asn Pro Ser Asn Leu Val
            355                 360                 365

Gln Val Ile Leu Asn Gly Val Gln Arg Lys Ile Gly Ser Glu Asp Ile
        370                 375                 380

Gly Met Pro Ala Phe Arg Tyr Asp Leu Asn Asp Ala Gln Ile Ala Ala
385                 390                 395                 400

Leu Thr Asn Tyr Val Thr Ala Gln Phe Gly Asn Pro Ala Ala Lys Val
            405                 410                 415

Thr Glu Gln Asp Val Ala Lys Leu Arg
        420                 425

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Gly Gly Gly Ser
1               5

<210> SEQ ID NO 6
<211> LENGTH: 7
<212> TYPE: PRT
<213> ORGANISM: Artificial Sequence
<220> FEATURE:
<223> OTHER INFORMATION: partial sequence

<400> SEQUENCE: 6

Gln Asp Val Ala Lys Leu Arg
1               5

<210> SEQ ID NO 7
<211> LENGTH: 4
<212> TYPE: PRT
<213> ORGANISM: Artificial Sequence
<220> FEATURE:
<223> OTHER INFORMATION: partial sequence

<400> SEQUENCE: 7

Met Ala Ser Gln
1

<210> SEQ ID NO 8
<211> LENGTH: 4
<212> TYPE: PRT
<213> ORGANISM: Artificial Sequence
<220> FEATURE:
<223> OTHER INFORMATION: partial sequence

<400> SEQUENCE: 8

Asp Ala Ala Pro
1

<210> SEQ ID NO 9
<211> LENGTH: 8
<212> TYPE: PRT
<213> ORGANISM: Artificial Sequence
```

```
<220> FEATURE:
<223> OTHER INFORMATION: His tag

<400> SEQUENCE: 9

Gly Ser His His His His His
1               5
```